United States Patent [19]
Di Vita

[11] 4,349,276
[45] Sep. 14, 1982

[54] METHOD OF AND SYSTEM FOR DETERMINING REFRACTIVE-INDEX PROFILES OF OPTICAL FIBERS

[75] Inventor: Pietro Di Vita, Turin, Italy

[73] Assignee: Cselt-Centro Studi e Laboratori Telecomunicazioni S.p.A., Turin, Italy

[21] Appl. No.: 208,705

[22] Filed: Nov. 14, 1980

[30] Foreign Application Priority Data

Nov. 15, 1979 [IT] Italy ................................ 69212 A/79

[51] Int. Cl.³ ...................... G01N 21/84; G01N 21/41
[52] U.S. Cl. .................................... 356/73.1; 356/128
[58] Field of Search ............................... 356/73.1, 128

[56] References Cited
PUBLICATIONS
"Practical Application of the Refracted Near-Field Technique for the Measurement of Optical Fibre Refractive Index Profiles", White, Optical and Quantum Electronics 11, (1979), pp. 185–196.

Primary Examiner—Vincent P. McGraw
Attorney, Agent, or Firm—Karl F. Ross

[57] ABSTRACT

To facilitate determination of the refractive-index profile of an optical fiber by the near-field technique, the fiber to be examined is inserted into a body of transparent liquid held by surface tension in a surrounding capillary tube also made of light-transmissive material. The tube, which is axially coextensive with the inserted fiber, has a refractive index less than the minimum index of the fiber core and cladding whereas the liquid has a refractive index exceeding the maximum index of the fiber core.

7 Claims, 3 Drawing Figures

METHOD OF AND SYSTEM FOR DETERMINING REFRACTIVE-INDEX PROFILES OF OPTICAL FIBERS

FIELD OF THE INVENTION

My present invention relates to a method of and a system for determining the refractive-index profile of an optical fiber.

BACKGROUND OF THE INVENTION

One of the most convenient methods of determining such a refractive-index profile is the so-called near-field technique which measures the luminous energy at the output end of the fiber whose input end is being illuminated from a light source of uniform radiance (known as a Lambertian source), with suppression of slanting leaky-mode rays so that practically all the incident light is internally reflected by the sheath or cladding of the fiber core and is thus transmitted to the opposite end. The power distribution I(r) along a radius of the fiber, as determined by a scanning of its output end, is then given by $$I(r) = k[n^2(r) - n_e^2] \qquad (1)$$

where n(r) is the refractive index at a given distance from the fiber axis, $n_e$ is the index of the cladding surrounding the core, and k is a proportionality factor.

The suppression of leaky-mode rays is a relatively simple matter when the fiber has a stepped profile, i.e. when its refractive index varies discontinuously in the radial direction; in that case the undesired rays all have an angle of incidence exceeding a predetermined value and can thus be eliminated with the aid of a suitable diaphragm. In the case of a graded or continuously varying profile, on the other hand, these leaky rays are practically inseparable from guided rays commingled therewith. Reference in this connection may be made to an article by K. I. WHITE in *Optical and Quantum Electronics* 11 (published 1979 by Chapman & Hall Ltd. in Great Britain), pages 185–196, titled "Practical application of the refracted near-field technique for the measurement of optical fibre refractive index profiled".

Another problem arising with this near-field technique is the fact that, in conformity with equation (1), a refractive index n(r) which is lower than the cladding index $n_e$ at any radius of the fiber core cannot be measured. The formula also fails with fibers of very small cross-section transmitting only in a single mode or in a low number of modes.

The above-identified Paper by K. I. White discusses an alternative method of determining the refractive-index profile, referred to as a "refracted near-field techinque", which measures light lost instead of transmitted power and thus also takes the leaky rays into consideration. That method, however, requires certain adjustments to compensate for lack of precise linearity which must be determined empirically and are therefore not readily reproducible.

OBJECTS OF THE INVENTION

Thus, an important object of my present invention is to provide a method of utilizing the near-field technique for determining the refractive-index profile of an optical fiber which does not necessarily satisfy all the aforementioned prerequisites for the conventional use of that technique.

A related object is to provide a simple system for practicing this improved method.

SUMMARY OF THE INVENTION

The method according to my present invention, applicable to any fiber whose core has a refractive index within a predetermined range and whose cladding has an index near but not necessarily beneath the lower limit of that range, comprises the steps of inserting the fiber to be examined into an axially coextensive capillary tube of transparent material with a refractive index less than the lower limit of the core-index range, filling an annular clearance between the tube and the fiber with a transparent liquid having a refractive index above the upper limit of that range, illuminating an end of the resulting unit, photoelectrically scanning the opposite end of this unit in a manner known per se to measure the luminous energy emitted along a radius thereof, and registering the values so measured.

A system for carrying out this method comprises optical means for focusing rays from a source of noncoherent light into a convergent beam centered on the axis of the capillary tube surrounding the fiber to be examined so as to provide substantially uniform illumination of an input end of the unit consisting of the tube, the fiber and the intervening liquid, photoelectric means positioned to scan the opposite end of that unit along a radius thereof for converting luminous energy received therefrom into electrical signals, and evaluation means connected to the photoelectric means for registering these electrical signals.

The three-component unit referred to may be considered a modified light guide whose sheath, represented by the capillary tube, has a refractive index invariably lower than that of any part of its central body constituted by the fiber and the liquid; the nonhomogeneous character of that composite structure insures the existence of a stepped profile enabling suppression of leaky-mode rays by a diaphragm interposed in the light path of the source, while the relatively large diameter of the structure establishes multimode transmission even with a very thin fiber. Thus, the signals generated by the photoelectric scanner can be correctly evaluated according to the foregoing equation (1).

BRIEF DESCRIPTION OF THE DRAWING

The above and other features of my invention will now be described in detail with reference to the accompanying drawing in which.

SPECIFIC DESCRIPTION

Figure 1:
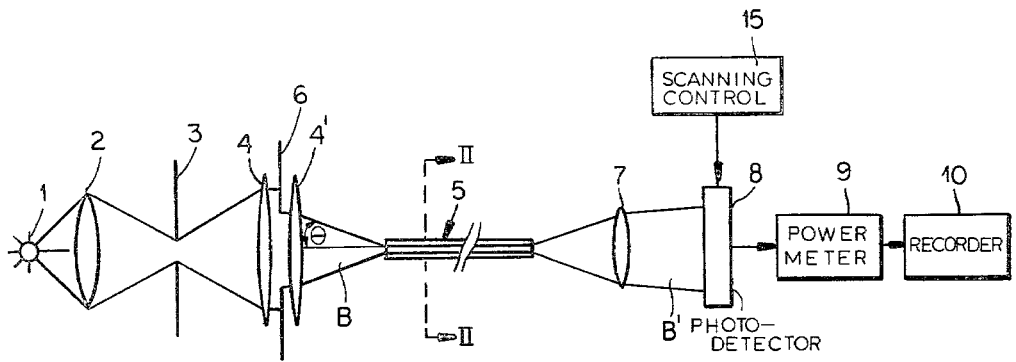
FIG. 1 is a diagrammatic representation of a partly conventional system for measuring the refractive-index profile of an optical fiber in accordance with my present invention.

In FIG. 1 I have shown a source 1 of noncoherent light, such as a tungsten-halogen lamp, whose rays are collected by a condenser lens 2 and focused upon a pinhole of a diaphragm 3 which thus becomes a virtual point source. A microscope objective, represented by two further lenses 4 and 4', intercepts the rays passing the diaphragm 3 and concentrates them into a convergent beam B whose vertex angle $2\theta$ is limited by another diaphragm 6 interposed between these lenses. Beam B impinges upon an end face of a cylindrical light-guiding unit 5, more fully described hereinafter with reference to FIG. 2, whose opposite end emits luminous energy onto a photodetector 8 through another microscope objective represented by a single convergent lens 7. Detector 7 scans the beam B' of substantially parallel rays issuing from unit 5, under the control of a conventional circuit 15, and delivers signals proportional to luminous intensity to a power meter 9 feeding a recorder 10.

Figure 2:
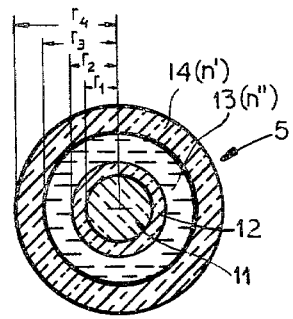
FIG. 2 is a cross-sectional view of a composite structure including the fiber to be examined, taken on the line II—II of FIG. 1 but drawn to a greatly enlarged scale.

As shown in FIG. 2, unit 5 consists of an optical fiber with a core 11 and cladding 12, a capillary tube 14 coaxially surrounding that fiber, and a liquid 13 which is held by surface tension in an annular space present between cladding 12 and tube 14. This tube, whose length is many times greater than its diameter as seen in FIG. 1, is axially coextensive with fiber 11, 12 and with the liquid filling 13 so that all components of unit 5 terminate in two transverse planes at its input and output ends. The radii of the outer peripheries of core 11, cladding 12, filling 13 and tube 14 have been respectively designated $r_1$, $r_2$, $r_3$ and $r_4$.

Tube 14 consists of a transparent material--e.g. glass doped with boron or fluorine, or a plastic--whose refractive index n' lies below the range within which the index of fiber 11, 12 may vary, the fiber material being usually quartz. Liquid 13, on the other hand, has a refractive index n" lying well above that range; suitable liquids of this type include glycerol, various oils (e.g. linseed, almond, sandalwood, lemon or clove), cinnamon aldehyde, iodo-naphthalene, potassium and mercury iodides, methylene iodide with sulfur, carbon sulfide, benzene, and a number of other compounds commonly used in refractometric tests or as index-matching fluids.

Figure 3:
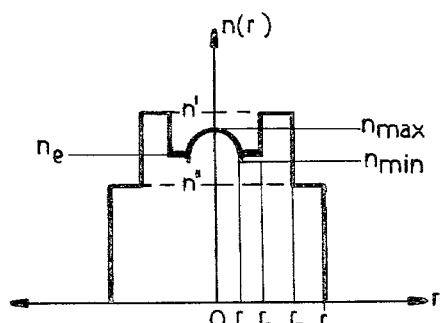
FIG. 3 is a graph showing refractive index plotted against a radius of the structure of FIG. 2.

In order to suppress leaky-mode rays in beam B, the angle of incidence $\theta$ of that beam is limited by diaphragm 6 to a value given by $$\theta = \arcsin \sqrt{n''^2 - n'^2} \tag{2}$$

provided that the light-guiding unit 5 is surrounded by air, as will usually be the case. Under these circumstances, recorder 10 will register a set of light-intensity values which may give rise to a refractive-index profile as shown in FIG. 3 where index n(r) has been plotted against radius r. The index of the fiber 11, 12 lies in a range limited by upper and lower values $n_{max}$ and $n_{min}$ which can be approximately predicted; index n' of liquid 13 exceeds the upper range limit $n_{max}$ while index n" of tube 14 is considerably less than the lower range limit $n_{min}$ in order to insure total internal reflection at the inner surface of tube 14.

In the example illustrated in FIG. 3, the index n(r) of the fiber core 11 progressively decreases from value $n_{max}$ at the axis (r=0) to value $n_{min}$ at radius $r_1$, this latter value being slightly less than the index $n_e$ of cladding 12 between radii $r_1$ and $r_2$. Beyond that radius the profile has two distinct steps n' and n" enabling the elimination of leaky rays by diaphragm 6 in accordance with equation (2). The range width $n_{max}-n_{min}$ is close to the difference $n_{max}-n_e$ between the maximum core index and the cladding index; the latter index, being more readily ascertainable, may therefore be substituted for the lower range limit in the selection of a suitable value for the tube index n". Thus, I prefer to let index n" differ from the upper range limit $n_{max}$ by at least twice the difference $n_{max}-n_e$; this will give correct results even if index n(r) should drop below cladding index $n_e$ by as much as the difference $n_{max}-n_e$.

I claim:

1. A method of determining the refractive-index profile of an optical fiber having a core with a refractive index within a predetermined range sheathed by cladding with a refractive index near the lower limit of said range, comprising the steps of:
   (a) inserting the fiber to be examined into an axially coextensive capillary tube of transparent material with a refractive index less than the lower limit of said range while leaving an annular clearance between said tube and the fiber;
   (b) filling said annular clearance with a transparent liquid having a refractive index higher than the upper limit of said range;
   (c) illuminating an end of the resulting unit;
   (d) photoelectrically scanning the opposite end of said unit to measure the luminous energy emitted along a radius thereof; and
   (e) registering the values measured in step (d).

2. A method as defined in claim 1 wherein the illumination in step (c) is carried out with noncoherent light from a virtual point source focused into a converging beam of sufficiently limited vertex angle to suppress leaky-mode rays.

3. A method as defined in claim 1 or 2 wherein the refractive index of said tube differs from the maximum index of said core by at least twice the difference between said maximum index and the index of the cladding.

4. A system for determining the refractive-index profile of an optical fiber having a core with a refractive index within a predetermined range sheathed by cladding with a refractive index near the lower circuit of said range, comprising:
   a capillary tube of transparent material with a refractive index less than the lower limit of said range;
   a transparent liquid adhering to the inner wall surface of said tube and having a refractive index higher than the upper limit of said range, said liquid filling a clearance between said tube and an axially coextensive inserted fiber to be examined;
   a source of noncoherent light;
   optical means focusing light from said source into a convergent beam centered on the axis of said tube and trained upon an end thereof for illuminating same together with an end of the inserted fiber and the intervening liquid;
   photoelectric means positioned to scan the opposite end of said tube, said fiber and said liquid along a radius thereof and to convert luminous energy received therefrom into electrical signals; and
   evaluation means connected to said photoelectric means for registering said electrical signals.

5. A system as defined in claim 4, further comprising diaphragm means interposed in the light path of said source for limiting said convergent beam to a vertex angle suppressing leaky-mode rays.

6. A system as defined in claim 5 wherein said diaphragm means establishes a maximum angle of incidence for said converging beam equal at most to the arc sine of the square root of the difference between the squares of the refractive indices of said liquid and said tube.

7. A system as defined in claim 5 or 6 wherein said diaphragm means is bracketed by two convergent lenses forming part of said optical means.

* * * * *